United States Patent [19]

Sands

[11] Patent Number: 4,798,788
[45] Date of Patent: Jan. 17, 1989

[54] PROCESSES AND MATERIALS FOR CARRYING OUT MICROCHEMICAL AND MICROBIOLOGICAL TESTS

[76] Inventor: Thomas J. Sands, 40 Naseby Close, Wellingborough, Northants, NN8 3XB, England

[21] Appl. No.: 833,389
[22] PCT Filed: Jun. 24, 1985
[86] PCT No.: PCT/GB85/00278
    § 371 Date: Feb. 20, 1986
    § 102(e) Date: Feb. 20, 1986
[87] PCT Pub. No.: WO86/00341
    PCT Pub. Date: Jan. 16, 1986

[30] Foreign Application Priority Data

Jun. 22, 1984 [GB] United Kingdom ............... 8416044

[51] Int. Cl.$^4$ .................. C12Q 1/12; C12Q 1/02; C12Q 1/04
[52] U.S. Cl. ....................... 435/37; 435/29; 435/34; 435/810; 436/110; 436/172; 436/903
[58] Field of Search .......... 435/29, 34, 37, 253, 435/810; 436/110, 172, 903

[56] References Cited

U.S. PATENT DOCUMENTS 3,785,929  1/1984  Kronish ................ 435/37
4,434,235  2/1984  Rabi et al. ............ 435/37

OTHER PUBLICATIONS

Coppola et al., "Nitrite in Meat Products Determined by Fluorescence Quenching of p-Aminobenzoate Ion", Journal of the AOAC (vol. 59, No. 4, 1976), pp. 783-786.
Coppola et al., (1976) in Chemical Abstracts vol. 85, No. 17, p. 121919, Item No. 121908r.

Primary Examiner—Robert J. Warden
Assistant Examiner—Jack Spiegel
Attorney, Agent, or Firm—Ostrolenk, Faber, Gerb & Soffen

[57] ABSTRACT

A microbiological culture test process for detecting the presence of nitrate-reducing microorganisms in an inoculum sample, which comprises (a) culturing a microorganism to be tested in the presence of adequately nitrite-free nitrate, for a period sufficient to allow reduction of nitrate by any microorganism (if present) that has the capacity to reduce nitrate to nitrite, (e.g. 1-6 hours);

(b) exposing the culture medium after culture to (diazotizing) acid conditions in the presence of an amino-containing fluorophor thereby to cause diazotization of the fluorophor to the extent of any nitrite present in the medium to form a diazonium derivative (or further reaction product thereof) which is substantially less fluorescent (or fluoresces at a substantially different wavelength) than said amino-containing fluorophor, and (c) assessing the fluorescence of the culture medium as treated by step (b), thereby to show a reduction in fluorescence in the presence of a nitrate-reducing microorganism.

13 Claims, No Drawings

PROCESSES AND MATERIALS FOR CARRYING OUT MICROCHEMICAL AND MICROBIOLOGICAL TESTS

This invention relates to processes and materials for carrying out microchemical and microbiological tests. In particular, it relates to chemical tests to detect the presence of small quantities of nitrite, and the application of such tests to detecting the production of nitrite by microorganisms in culture, e.g. by reduction of nitrate supplied in the culture medium.

A well established test for small quantities of nitrite is known as the Griess test. This test relies on treating an aqueous material suspected of containing nitrate with p-aminobenzenesulphonic acid in strong acid solution (e.g. 5 N acetic acid) and with alpha-dimethylaminoaphthalene, also in strong acid solution.

In the presence of nitrite the test develops a red dye colour, but no colour is given if the test is carried out with a nitrite-free sample.

This test is widely applied as part of a technique for the species identification and classification of bacteria by their cultural application in many clinical microbiology laboratories. The test can also be used to detect traces of nitrite in other samples, e.g. water samples to be analysed in public health laboratories.

As it stands, this test generally requires visual assessment of colour development, and it involves the use and handling of two aromatic amine reagents which are somewhat noxious and chemically closely related to known carcinogens.

The aim of this invention is to provide a nitrite test that can be assessed by fluorescence in the resulting test material. It is also the aim of the invention to provide tests that can give a fluorescent result in a form suited to automatic fluorometric assessment, especially for example by fluorometry that uses similar excitation and emission wavelengths as other and possibly hitherto chemically unrelated microbial tests, which can therefore be assessed simultaneously or in the same batch by similar or the same instrumentation. A further aim of the invention is to provide nitrite detection tests adapted to microbiological use for assessment of the nitrate-reducing capacity of microbial cultures, e.g. to assist in their identification, in which the use of noxious reagents to develop a colour result is minimised or avoided.

According to the present invention, nitrite is detected in a sample possibly containing small quantities of nitrite, especially for example an aqueous sample, such as for example a suspension or culture of microorganisms cultured in the presence of adequately nitrite-free nitrate for a period that allows reduction of nitrate, if possible, or a specimen of groundwater, by contacting the sample under acid conditions with a small quanity of an acid-stable fluorophor which has a content of amino groups, and in which the amino groups contribute substantially to the fluorescence, thereby to cause reaction between the amino groups of the fluorophor and any nitrite present under the acid conditions, and assessing the presence or quantity of nitrite by change in the fluorescence of the fluorophor as a result of the reaction.

A microbiological culture test process according to the invention, for detecting the presence of nitrate-reducing microorganisms is an inoculum sample, which comprises:

(a) culturing a microorganism to be tested in the presence of adequately nitrite-free nitrate, for a period sufficient to allow reduction of nitrate by any microorganism (if present) that has the capacity to reduce nitrate to nitrite (e.g. 1–6 hours);

(b) exposing the culture medium after culture to (diazotising) acid conditions in the presence of an amino-containing fluorophor thereby to cause diazotisation of the fluorophor to the extent of any nitrite present in the medium to form a diazonium derivative (or further reaction product thereof) which is substantially less fluorescent (or fluoresces at a substantially different wavelength) than said amino-containing fluorophor, and (c) assessing the fluorescence of the culture medium as treated by step (b), thereby to show a reduction in fluorescence in the presence of a nitrate-reducing microorganism.

Preferably the fluorophor is one which itself fluoresces under acid conditions but of which the acid reaction product with nitrite is substantially non-fluorescent under acid conditions, and the fluorescence is assessed or measured while the product is still under the acid conditions.

A suitable example of a fluorophor which can be used for this invention is an amino derivative of coumarin or flavone, for example a 7-amino coumarin (or a 3-amino-flavone), especially for example 7-amino-4-methyl coumarin (hereafter referred to as MCA).

It is believed that the test exploits the difference in fluorescence between the added amine reagent and its corresponding diazonium derivative formed during the test in the presence of nitrite under acid conditions.

The diazotising acid conditions can be achieved for example by acidifying the aqueous mixture of the sample to be tested and the fluorophor up to 2N–3N concentration of e.g. a strong or moderately strong acid, such as hydrochloric acid or acetic acid.

In a microbiological test for nitrate reduction, using the above-described method for detecting nitrite, suitable conditions are for example as follows.

EXAMPLE

A microbial inoculum is prepared containing about $10^7$ organisms per ml (final concentration) and the following further ingredients in the final concentrations noted:

Oxoid nutrient broth No. 2 (Trade Mark): 25g/l
Potassium nitrate (nitrite-free): 1g/l
Sodium chloride: 8.5g/l
MCA (7-amino-4-methyl coumarin): 15 μM, (equivalent to 2.64 mg/l).

It is convenient to handle a standardised quantity of 100 μl in each test sample.

Of course, the other materials present in the culture broth, and any other reagents, are chosen from those that do not already lead to quenching of the relevant fluorescence irrespective of the progress of the diazotising reaction.

This inoculum and broth-reagent mixture is incubated at 37° C. for a period within the range of about 1 hour to about 6 hours, and then acidified using a drop of 5N acetic acid solution.

After a short further period, the fluorescence of a test mixture can be compared with the fluorescence of control mixtures, and any substantial diminution in fluorescence can be taken to indicate the presence of nitrite produced by the microorganism by reduction of nitrate.

If the test mixture is incubated for much longer than 6 hours, e.g. overnight for about 18 hours, then it is possible for certain nitrate-reducing microbes to denitrify the nitrite further to nitrogen. In such a case the test will not give a diminution in fluorescence to indicate the presence of nitrite. However, as with the traditional test, these denitrifying organisms can be distinguished from the nitrate non-reducers by adding to the acid test mixture, after assessment has shown a lack of nitrate, a reducing agent that will itself reduce nitrate to nitrite (such as zinc dust under acid conditions). Residual nitrate will then, if present, be reduced to nitrite and give the characteristic diminution of fluorescence. Failure of the test to show a diminution of fluorescence even after addition of the external reducing agent indicates consumption of both the nitrate and any nitrite produced from it, i.e. by the action of denitrifying organisms.

However, the preferred method of carrying out the tests to incubate the inoculum mixture only for about 1–6 hours, during which shorter periods we find that even denitrifying organisms do not eliminate the nitrite so far produced: under these conditions both denitrifying and non-denitrifying nitrate-reducers give similar nitrite-positive results.

It is considered to be advisable, in carrying out several embodiments of the test herein described, to avoid realkalizing the acid test mixture before measuring or assessing its fluorescence, to avoid the possible development of other interfering sources of fluorescence in this mixtures.

It can be seen from the above description that the invention provides a method of nitrite detection or estimation and a method of detecting the property of nitrate reduction in microorganisms: the invention also comprises materials for carrying out such tests. In particular, the materials can comprise a microbiological broth containing (besides usual microbial culture medium ingredients) (adequately nitrite-free) nitrate and the amino-containing fluorophor in suitable quantities (for example the quantities given in detail above), to be used in association with an acidifying reagent, such as the examples given above. If desired, a convenient embodiment can be used in which the indicated broth constituents, (or a selection of them including the essential nitrate, and optionally also the fluorophor), can be presented in dry form in one or more wells of a prepared (usually sterile) microtitre tray for use in carrying out microbial culture tests (usually protected by a removable adhesive sealing cover). An alternative dry form presents some or all of the materials in or associated with (usually sterile) containers for preparing a microbial inoculum suspension, e.g. a bottle or other container with a dry preparation of the materials contained therein; or a closure for such a bottle, such as a screw cap, with a dry preparation of the materials carried on a surface which in use is to contact the inoculum so that the materials may be dispersed therethrough, such as the inner surface of the screw cap or the surface of a wad placed within the screw cap; or in a dry form on a carrier material suitable to be added to such an inoculum or to a culture well, so that the materials are dispersed through the inoculum or culture suspension, such as strips or discs of paper or other cellulosic or non-cellulosic, fibrous or non-fibrous carrier sheet material.

All such preparations are desirably maintained dry and sterile before use, e.g. sealed within sterile foil sealing or packaging material.

One of the special advantages of the processes described herein is that the nitrate reduction test gives a fluoroscopic/fluorometric result that can be measured optically with the same excitation/emission wavelengths as a number of other (known in themselves) microbial culture tests (e.g. in the presence of various quantities or types of antimicrobial) giving a variably fluorescent result: e.g. culture tests in which a fluorogenic substrate such as 4-methyl umbelliferone phosphate or other ester and/or an aminoacyl or peptidyl 7-amino-4-methyl coumarin is hydrolysed to fluorophor during growth of the microorganism if this growth occurs.

Accordingly, combination tests including cultures for nitrate reduction testing and such antimicrobial culture tests are also included within the scope of the invention.

Other modifications and variations within the scope of the described invention will be apparent to the skilled reader as a result of reading the above disclosure, and the several features described by way of example can be presented in any desired combinations.

I claim:

1. A microbiological culture test process for detecting the presence of nitrate-reducing microorganisms in an inoculum sample, which comprises
   (a) culturing a microorganism to be tested in the presence of substantially nitrate-free nitrate and of a diazotizable amino-containing fluorophor selected from the group consisting of coumarins and flavones, for a period sufficient to allow reduction of nitrate by said microorganism having the capacity to reduce nitrate to nitrite,;
   (b) exposing the culture medium after culture to diazotizing acid conditions thereby to cause diazotization of the fluorophor to the extent of any nitrite present in the medium to form a diazonium derivative which is substantially less fluorescent at a predetermined wavelength at which said fluorophor is fluorescent than said amino-containing fluorophor when assessed for fluorescence under said acid conditions, and
   (c) assessing the fluorescence of the culture medium as treated by step (b) at said predetermined wavelength under the acid conditions established in step (b), thereby to detect presence of a nitrate-reducing microorganism by showing a reduction in fluorescence.

2. A process according to claim 1 in which the fluorophor is a fluorescent amino-coumarin.

3. A process according to claim 2, in which the fluorophor is 7-amino-methyl coumarin.

4. A process according to claim 1, wherein the microorganism is cultured in the presence of nitrite-free potassium nitrate.

5. A process according to claim 1, wherein the acid conditions of step (b) are produced by adding acid to the culture to give an acid concentration in the range about 2N–3N.

6. A process according to claim 5 in which the acid is hydrochloric acid or acetic acid.

7. A process according to claim 1 in which the culturing step (a) is conducted for a period of 1 to 6 hours.

8. A process according to claim 7 in which the phosphor is a fluorescent amino-coumarin, the microorganism is cultured in the presence of nitrate-free potassium nitrate and the acid conditions of step (b) are produced by adding acid to the culture to give an acid concentration in the range of about 2N–3N.

9. A process according to claim 8 in which the fluorophor is 7-amino-4-methyl coumarin and the acid is hydrochloric acid or acetic acid.

10. A microbial culture test medium for detecting nitrate-reducing microorganisms, comprising microbial culture medium which is substantially nitrite-free, a nitrate source, and a diazotisable amino-group-containing fluorophor selected from the group consisting of coumarins and flavones, wherein said fluorophor yields reduced fluorescence in the diazotised state when measured at a predetermined wavelength under diazotising acid conditions.

11. A microbial culture test medium according to claim 10, wherein said fluorophor is a fluorescent amino-coumarin.

12. A microbial culture test medium according to claim 11, wherein said fluorophor is 7-amino-4-methyl coumarin.

13. A test kit for detecting nitrate-reducing microorganisms,
comprising a prepared test tray with a plurality of receptacles, wherein at least one receptacle contains microbial inoculation medium, and, in dry form, nitrite-free nitrate, and diazotisable amino-group-containing fluorophor selected from the group consisting of coumarins and flavones which yield reduced fluorescence in the diazotised state when measured at a predetermined wavelength under diazotising acid conditions.

* * * * *